United States Patent [19]

Cameron

[11] Patent Number: 5,135,501
[45] Date of Patent: Aug. 4, 1992

[54] MATERIAL FOR THROUGH THE NEEDLE CATHETER

[75] Inventor: Robert Cameron, Tampa, Fla.

[73] Assignee: Ethicon, Inc., Somerville, N.J.

[21] Appl. No.: 623,131

[22] Filed: Dec. 6, 1990

[51] Int. Cl.⁵ ............................................. A61M 5/178
[52] U.S. Cl. ...................................... 604/161; 604/158
[58] Field of Search ................. 604/264, 160, 158, 161

[56] References Cited

U.S. PATENT DOCUMENTS

| | | | |
|---|---|---|---|
| 3,598,118 | 8/1971 | Warren | 604/160 X |
| 3,611,965 | 10/1971 | Lange | 604/161 |
| 3,746,683 | 7/1973 | Salyer et al. | 604/280 X |
| 4,354,491 | 10/1982 | Marbry | 604/160 |
| 4,557,724 | 12/1985 | Gregonis et al. | 604/265 X |
| 4,589,873 | 5/1986 | Schwartz et al. | 604/265 |
| 4,627,844 | 12/1986 | Schmitt | 604/264 |
| 4,666,437 | 5/1987 | Lambert | 604/265 |
| 4,846,812 | 7/1989 | Walker et al. | 604/265 X |
| 4,872,867 | 10/1989 | Joh | 604/269 |
| 4,876,126 | 10/1989 | Takemura | 604/266 X |
| 4,898,591 | 2/1990 | Jang et al. | 604/264 X |
| 4,906,238 | 3/1990 | Greenfeld et al. | 604/265 X |
| 4,955,895 | 9/1990 | Sugiyama et al. | 604/102 X |
| 4,964,853 | 10/1990 | Sugiyama et al. | 604/102 X |
| 4,994,047 | 2/1991 | Walker et al. | 604/264 |

*Primary Examiner*—John J. Wilson
*Assistant Examiner*—Jeffrey A. Smith
*Attorney, Agent, or Firm*—Paul A. Coletti

[57] ABSTRACT

A through the needle catheter is provided where the needle is splittable after removal and the catheter material is formed from an extremely hydrophilic polymer. Upon removal of the needle, the catheter expands with contact to water and other aqueous solutions, such as blood or intravenous dosages. Upon expansion, the outer diameter of the catheter tube seals the tube within the body tissue preventing leakage from the body tissue around the tube. Also, the inner diameter of the catheter tube expands to allow higher infustion flow rates of intravenous fluids into the body.

6 Claims, 2 Drawing Sheets

MATERIAL FOR THROUGH THE NEEDLE CATHETER

FIELD OF THE INVENTION

This invention relates to catheters for use in intravenous medication devices. Specifically, this invention relates to catheters which are placed into the body through a needle. Most specifically, this invention relates to material for use in catheters that are emplaced into the body within a needle.

BACKGROUND OF THE INVENTION

Intravenous catheters come in basically two forms. First, there are catheters which are emplaced over the introducer needle. After emplacement of the catheter the needle is withdrawn from the center of the catheter and intravenous transfusion is possible. The second type are catheters commonly referred to as "through the needle" catheters. In these devices, the needle is emplaced into the vein with the catheter inserted inside the hollow needle. After insertion, the needle is withdrawn, usually by splitting the needle apart during withdraw. Thus, the catheter remains within the vein and is able to transfuse immediately upon emplacement of the needle.

Through the needle catheters have one very distinct advantage. That is, through the needle catheters are quite easy to insert into the vein because only the needle itself has to be inserted through body tissue. Whereas known needle making techniques afford easy insertion of the through the needle catheter, catheters themselves are somewhat more difficult to insert into the body when they are exposed around the needle. Thus, where possible, through the needle catheters have preference.

In contrast, through the needle catheters have two major disadvantages. Removal of the needle is difficult. Because the needle is generally configured to be smaller than the catheter hub, the catheter must be disassembled, or disconnected from the catheter hub so that removal of the needle may take place. Then, the catheter is reassembled to the catheter hub from which infusion was possible.

On the other hand, removal may be possible by sliding the needle over the hub connection. This method is less than desirable because the size of the needle increased. Or, the needle could be left in place and the catheter left to remain within the needle during infusion. This is undesirable because it causes reduced catheter size and left a foreign object within the body during infusion. This difficulty has been overcome through use of needles splittable along their diameter, and then removable over the catheter hub.

Second, since the catheter tubing must necessarily be smaller than the inner diameter of the needle in a through the needle catheter, the catheter itself presented problems. First, as previously discussed, the catheter maintained a low flow rate. The design of the needle necessarily limited the tube dimensions so that the inner diameter of the tubing became even smaller than the needle, causing such low rates of flow. On the other hand, because such tubing is smaller than the needle outside diameter, after needle removal the catheter may create a poor seal between the catheter outside diameter and the pierced body tissue. This results in leakage problems in the tissue outside the catheter.

SUMMARY OF THE INVENTION

It is an object of the invention to provide a catheter which prevents leakage caused by improper seal with body tissue.

It is further an object of the invention to provide a through the needle catheter which has enhanced flow rate.

It is yet another object of the invention to provide a through the needle catheter in which insertion of the catheter remains simple and easy while overcoming the aforesaid problems of through the needle catheters.

It is yet another object of the invention in which removal of the needle in this through the needle catheter causes no patient discomfort or tissue trauma while overcoming the aforesaid problems of through the needle catheters.

Finally, it is an object of the invention to provide an improved through the needle catheter which is adaptable to all areas of catheter use.

These, and other objects of the invention, are accomplished in a through the needle catheter tube comprised of an extremely hydrophilic polymer which swells and softens upon continuous exposure to water or other aqueous solutions, such as blood and intravenous delivery systems. The improved catheter tube is introduced into the body within the inside diameter of a splittable needle so that the needle is removable upon insertion of the catheter. Upon removal of the needle and during catheter contact with water or other aqueous solutions, the catheter swells so that the catheter tube creates a better seal with the body and eliminates leakage possibilities.

In addition, because the catheter tube swells, the inside diameter of the tube increases and therefore the flow rate capabilities of the catheter tube are increased. Because the tube is formed from a hydrophilic polymer, an extremely stiff catheter can be inserted through the needle, yet it becomes soft upon insertion into the body for excellent indwelling of the catheter within body tissue.

This catheter is useful in all sorts of through the needle catheter areas, such as peripheral intravenous catheters, arterial catheters, single and multilumen central lines, as well as catheters used to deliver drugs or fluids to areas other than the vascular system.

The invention as described above, will be better understood by the accompanying Detailed Description of the Drawings taken in conjunction with the Detailed Description of the Invention which follows.

DETAILED DESCRIPTION OF THE DRAWINGS

DETAILED DESCRIPTION OF THE INVENTION

Figure 1:
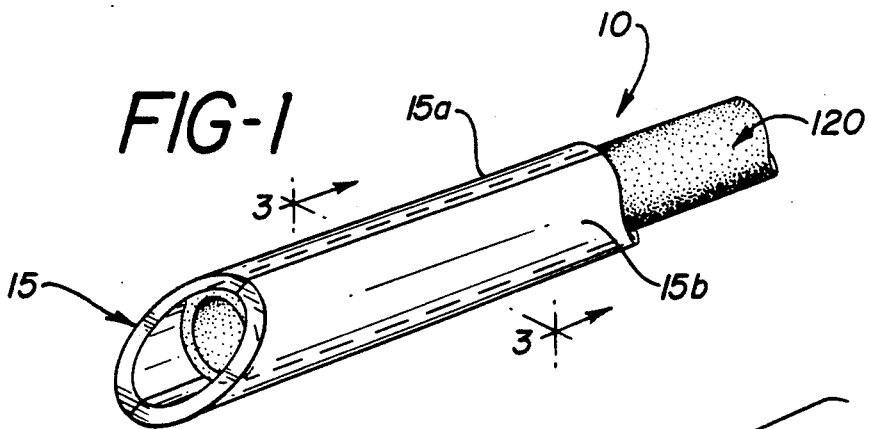
FIG. 1 is a perspective view of a typical through the needle catheter device as embodied in the invention.
Figure 2:
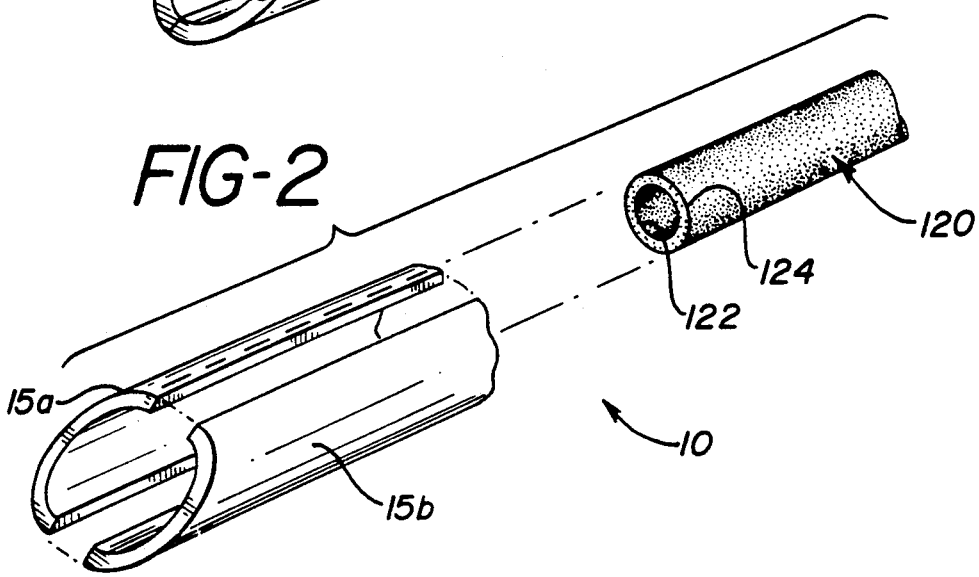
FIG. 2 is an exploded perspective view of FIG. 1.

As seen in FIGS. 1 and 2, a typical through the needle catheter device 10 comprises a catheter 120 having relatively rigid outer diameter 124 and relatively rigid inner diameter 122 connected to a catheter hub not shown which is ultimately attachable to a intravenous infusion device not shown. The catheter 10 outer diameter is smaller than the inner diameter of needle 15 into which the catheter is emplaced.

The needle 15 is usually attached to a needle hub not shown and is protected by a needle guard not shown before emplacement. In typical present day systems, the needle 15 is also splittable into two halves 15a, 15b along its lengthwise diameter. The needle 15 presents a hollow tubular configuration for insertion within body, and is better explained in U.S. Pat. Nos. 4,957,488 and 4,957,489 assigned to the common assignee of this invention, incorporated herein by reference.

Generally, typical catheters 120 have been formed from extremely stiff polymers which allow for rather simple insertion within the needle 15 and therefore within the body tissue. These catheters 120 also cause many of the problems encountered as described in the Background of this Invention. On the other hand, as seen in FIGS. 3, 4 and 5 and 6, the catheter tube of this invention differs from typical through the needle catheter tubes. The catheter tube of this invention is formed from an extremely hydrophilic polymer, such as poly HEMA (polyhydroxyethyl(methacrylate), crosslinked poly-ox (polyoxyethylene) and crosslinked polyvinyl pyrrolidone or their equivalents.

Figure 3:
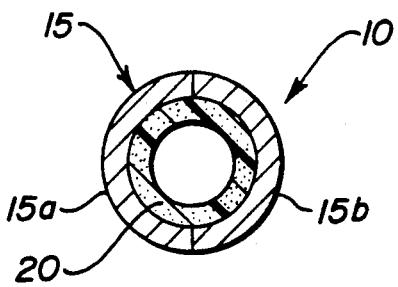
FIG. 3 is a cross-sectional view of the invention taken along lines 3—3 of FIG. 1.
Figure 4:
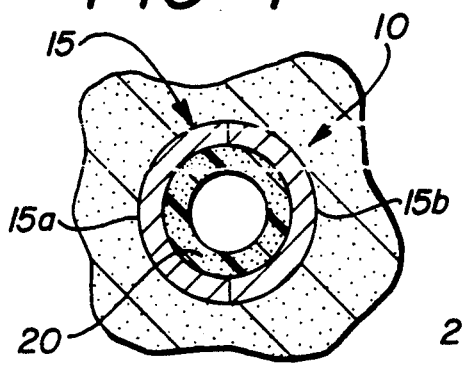
FIG. 4 is a cross-sectional view as in FIG. 3 showing the invention emplaced within body tissue.
Figure 7:
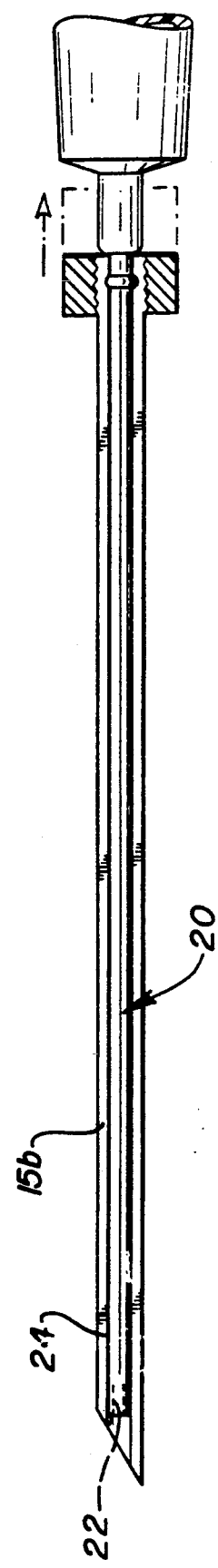
FIG. 7 is a view of the catheter of this invention attached to an infusion set.

Generally, these polymers are also stiff before wetting. All the benefits of typical through the needle catheters are still derived from this catheter when inserted through a needle into tissue. As with typical splittable needles, the needle 15 of this invention also is removable from the body tissue by splitting after insertion. Thus, while the catheter 20 is inserted into the body as seen in FIG. 3, and the needle 15 is originally in the tissue as seen in FIG. 4, the needle 15 is removed by splitting as seen in FIG. 2. Because the catheter 20 is still small and stiff, the needle readily slides over the catheter tube 20. FIG. 7 shows a catheter of this invention attached to an infusion set 200.

After insertion of the catheter 20 and removal of the needle 15 from the tissue, the hydrophilic aspects of the catheter tube 20 begin to take effect upon wetting, and the catheter tube 20 begins to expand. Upon expansion, the outer diameter of the catheter tube 20 grows to at least fit the evacuated area caused by the removal of the splittable needle 15. Thus, any leakage problems caused by difficiencies in the catheter outside diameter 24 are avoided.

Figure 5:
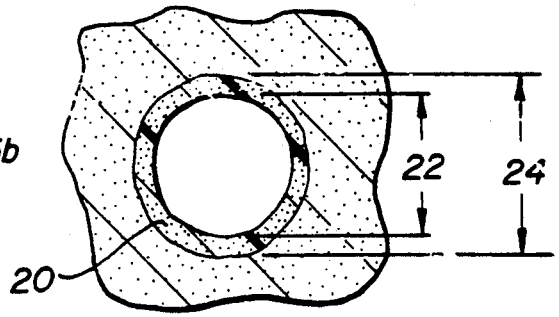
FIG. 5 is a cross-sectional view of the catheter as in FIG. 3 of the invention placed within body tissue with the splittable needle removed.
Figure 6:
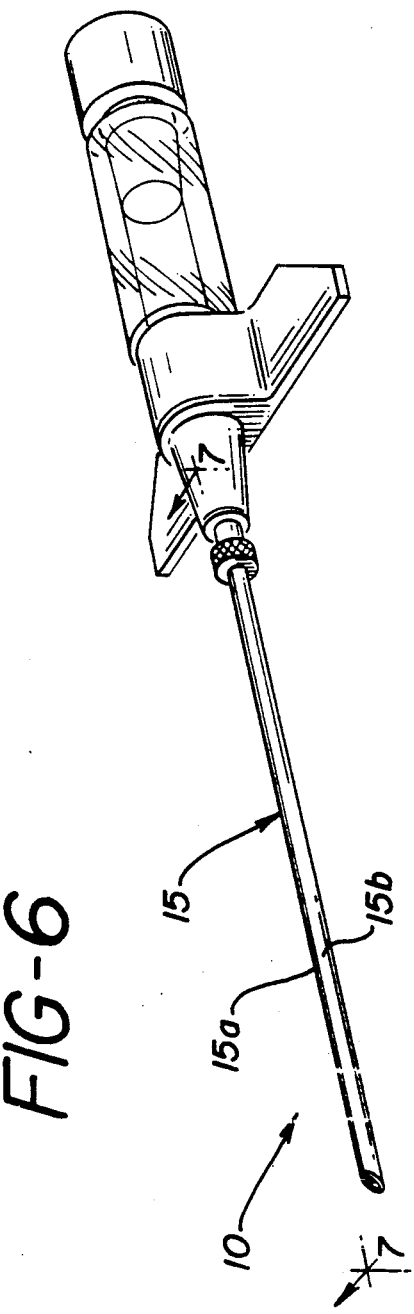
FIG. 6 is perspective view of the catheter of this invention before splitting the needle.

As seen in FIG. 5, after removal of the needle and growth of the catheter after wetting of the hydrophilic polymer, the inner diameter 22 of the catheter tube also begins to grow. With this expansion of the inner diameter 22 of the tube, there is constriction of flow rates for infusion. Therefore, infusion and flow problems are also no longer a difficulty. With a typical catheter tube, cross sectional area will increase by over 50%, improving flow rates by this amount.

Accordingly, with the improved material used in this catheter all the difficulties previously encountered by through the needle catheters are removed, allowing for a desirable use of through the needle catheters.

While this invention is described with respect to a particularly inferred embodiment, it is understood that the following claims and their equivalents are meant to more accurately describe the invention.

What is claimed is:

1. A catheter assembly comprising:
    a hollow needle splittable into two halves;
    a catheter removably inserted into the hollow needle and connectable to an infusion set;
    said needle removable from said catheter assembly after insertion into a patient, and wherein said catheter expands after removal of said needle, and said catheter formed from a material selected from the group consisting of polyhydroxyethyl (methacrylate), and crosslinked polyoxyethylene.

2. The assembly of claim 1 further including an infusion set and wherein the infusion set provides infusion immediately after insertion of said needle and during removal of said needle.

3. The assembly of claim 2 wherein said catheter is attached to a catheter hub attached to said infusion set.

4. The assembly of claim 3 wherein said catheter expands more than 50% in cross-section after wetting.

5. A catheter assembly comprising:
    a hollow needle splittable into two halves;
    a catheter insertable into the hollow needle and connectable to a infusion set;
    said needle removable from said catheter assembly after insertion into a patient, and wherein said catheter expands after removal of said needle, and said catheter formed from a hydrophilic polymeric material and wherein the catheter material is crosslinked polyoxyethlene.

6. A catheter assembly comprising:
    a hollow needle splittable into two halves;
    a catheter insertable into the hollow needle and connectable to an infusion set;
    said needle removable from said catheter assembly after insertion into a patient, and wherein said catheter expands after removal of said needle, and said catheter formed from a hydrophilic polymeric material and wherein the catheter material is polyhydroxyethyl (methacrylate).

* * * * *